(12) United States Patent
Vandenbark et al.

(10) Patent No.: US 10,525,101 B2
(45) Date of Patent: Jan. 7, 2020

(54) METHODS OF TREATING INFLAMMATORY OR AUTOIMMUNE DISORDERS WITH COMPOUNDS THAT BIND MACROPHAGE MIGRATION INHIBITORY FACTOR

(71) Applicants: Oregon Health & Science University, Portland, OR (US); The United States Government as represented by The Department of Veterans Affairs, Washington, DC (US)

(72) Inventors: Arthur A. Vandenbark, Portland, OR (US); Gil Benedek, Portland, OR (US); Roberto Meza-Romero, Beaverton, OR (US)

(73) Assignees: Oregon Health & Science University, Portland, OR (US); The United States Government as Represented by the Department of Veterans Affairs, Washington, DC (US)

( * ) Notice: Subject to any disclaimer, the term of this patent is extended or adjusted under 35 U.S.C. 154(b) by 81 days.

(21) Appl. No.: 15/331,612

(22) Filed: Oct. 21, 2016

(65) Prior Publication Data
US 2017/0114117 A1 Apr. 27, 2017

Related U.S. Application Data

(60) Provisional application No. 62/245,864, filed on Oct. 23, 2015.

(51) Int. Cl.
*A61K 38/10* (2006.01)
*A61K 38/17* (2006.01)
*C07K 14/74* (2006.01)
*A61K 38/00* (2006.01)

(52) U.S. Cl.
CPC ...... *A61K 38/1774* (2013.01); *C07K 14/70539* (2013.01); *A61K 38/00* (2013.01); *C07K 2319/00* (2013.01)

(58) Field of Classification Search
CPC ................................. C07K 14/70539
See application file for complete search history.

(56) References Cited

U.S. PATENT DOCUMENTS

| | | | |
|---|---|---|---|
| 2010/0183598 A1* | 7/2010 | Schultz | A61K 9/5084 514/1.1 |
| 2014/0178403 A1 | 6/2014 | Bucala et al. | |
| 2015/0098956 A1 | 4/2015 | Vandenbark et al. | |

FOREIGN PATENT DOCUMENTS

| | | |
|---|---|---|
| DE | 10228218 A1 | 2/2004 |
| WO | WO 02/00677 A1 | 1/2002 |
| WO | WO 2014/037419 A1 | 3/2014 |

OTHER PUBLICATIONS

Greven et al. Expert Opin. Ther. Targets 14(3): 253-264, 2010.*
Leng et al., "MIF Signal Transduction Initiated by Binding to CD74," *J. Exp. Med.* vol. 197, No. 11, pp. 1467-1476, 2003.
Meza-Romero et al., "Modeling of both shared and distinct interactions between MIF and its homologue D-DT with their common receptor CD74," *Cytokine*, vol. 88, pp. 62-70, 2016.
Meza-Romero et al., "Predicted structure of MIF/CD74 and RTL1000/CD74 complexes," *Metab Brain Dis*, vol. 31, pp. 249-255, 2016.

* cited by examiner

*Primary Examiner* — Christine J Saoud
(74) *Attorney, Agent, or Firm* — Klarquist Sparkman, LLP

(57) ABSTRACT

Recombinant polypeptides, pharmaceutical compositions comprising recombinant polypeptides, and methods of treating autoimmune and/or inflammatory diseases using the pharmaceutical compositions are disclosed. The polypeptides are based upon the trimerization and/or MIF binding domains of CD74.

14 Claims, 9 Drawing Sheets
Specification includes a Sequence Listing.

METHODS OF TREATING INFLAMMATORY OR AUTOIMMUNE DISORDERS WITH COMPOUNDS THAT BIND MACROPHAGE MIGRATION INHIBITORY FACTOR

CROSS REFERENCE TO RELATED APPLICATION

This claims the benefit of U.S. Provisional Application No. 62/245,864, filed Oct. 23, 2015, which is incorporated herein by reference in its entirety.

ACKNOWLEDGEMENT OF GOVERNMENT SUPPORT

Work resulting in this invention was supported by the United States government under the terms of Grant Number 5R01 NS047661, awarded by the National Institutes of Health, Grant Number RG-5068-A-6 and a Merit Review Grant awarded by the Department of Veterans Affairs. The United States government has certain rights to this invention.

FIELD

This disclosure relates to recombinant therapeutic proteins, particularly recombinant therapeutic proteins comprising particular sequences of CD74 and methods of their use.

BACKGROUND

CD74 is a chaperone that assists with the folding and trafficking of Class II MHC. It has a structure characterized by an un-structured domain near the N-terminus, with a more organized domain conformation at the C-terminus. This C-terminal domain trimerizes with other CD74 molecules. CD74 is the receptor for macrophage migration inhibitory factor (MIF).

SUMMARY

Disclosed herein are polypeptides derived from CD74 that can compete with recombinant T cell receptor ligands (RTLs) such as RTL1000 (described in U.S. Pat. No. 8,377,447 (2013); incorporated by reference herein) as well as partial MHC molecules such as a DRα1 (US 2015/0044245; incorporated by reference herein) for binding of the CD74 ligand macrophage migration inhibitory factor (MIF). The disclosed polypeptides are believed to have similar effects to RTL1000 and DRα1, without the need for any HLA subtyping.

Also disclosed are compositions including the disclosed polypeptides. In some embodiments, the compositions include at least a first polypeptide. In some examples, the first polypeptide comprises or consists of SEQ ID NO: 1 or SEQ ID NO: 3, including polypeptides comprising or consisting of SEQ ID NO: 2 or SEQ ID NO: 4. In additional embodiments, the composition further includes at least a second polypeptide. In some examples, the composition includes a first polypeptide comprising or consisting of SEQ ID NO: 1 and a second polypeptide comprising or consisting of SEQ ID NO: 3 (such as SEQ ID NO: 2 and SEQ ID NO: 4). In still further examples, the first polypeptide and the second polypeptide in the composition are covalently linked together, either directly or by a chemical or peptide linker that covalently links the first polypeptide and the second polypeptide. Examples of such polypeptides include SEQ ID NO: 11, SEQ ID NO: 12, SEQ ID NO: 13, SEQ ID NO: 14, SEQ ID NO: 15, or SEQ ID NO: 16. The polypeptide compositions can also include a polypeptide of SEQ ID NO: 5, either included in a mixture or linked to a first or second polypeptide.

Other recombinant polypeptide compositions include compositions comprising a first polypeptide comprising the sequence YGNMT (SEQ ID NO: 21) and a second polypeptide comprising the sequence RHSLE (SEQ ID NO: 22). Examples of such polypeptides include SEQ ID NO: 7 and SEQ ID NO: 9. Such polypeptides can further include a linker polypeptide that covalently links the first and second polypeptide. Examples of such a composition include SEQ ID NO: 17, SEQ ID NO: 18, or SEQ ID NO: 19.

Also disclosed are pharmaceutical compositions comprising an effective amount of the above recombinant polypeptide compositions.

Methods of treating an inflammatory or autoimmune disorder in a subject that involve administering the disclosed polypeptides or pharmaceutical compositions are also disclosed.

The foregoing and other features of the disclosure will become more apparent from the following detailed description, which proceeds with reference to the accompanying figures.

BRIEF DESCRIPTION OF THE DRAWINGS

FIG. 4A shows $IC_{50}$ 4.706 μM; R square 0.9736. FIG. 4B shows $IC_{50}$ no competitor: 7.432 μM, R square 0.1022; α-helix 1: $IC_{50}$ 34.96 μM, R square 0.9883; α-helix 2: $IC_{50}$ 24.47 μM, R square 0.7900.

SEQUENCE LISTING

Figure 1A:
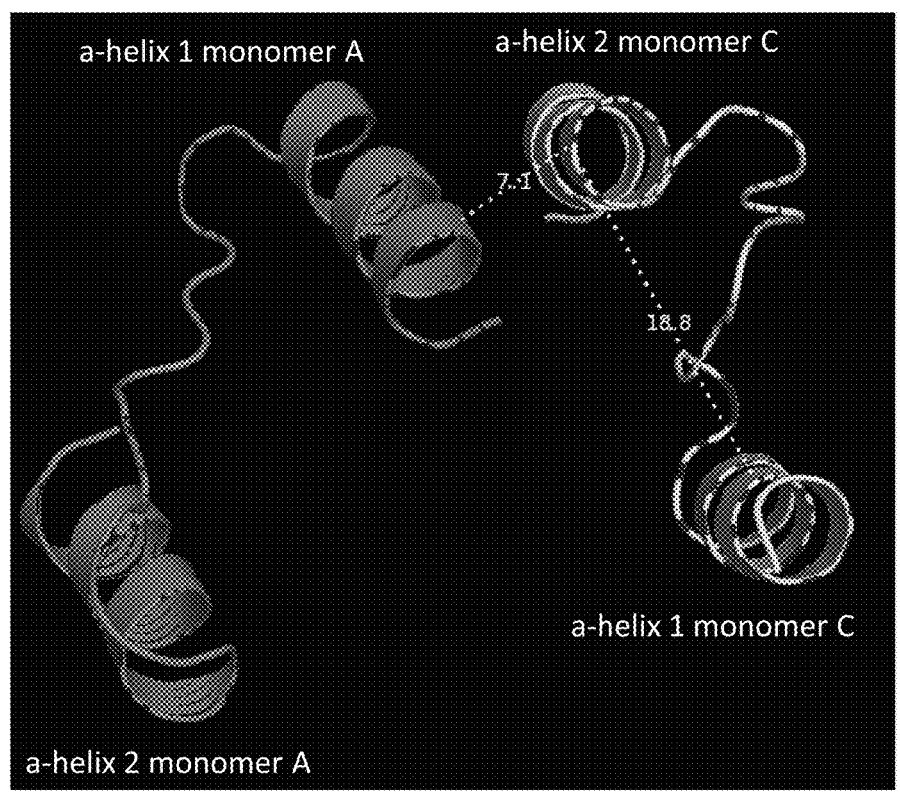
FIG. 1A is a representation of the α-helix 1 and α-helix 2 of the trimerization domain of CD74 in a ribbon diagram.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

The Sequence Listing is submitted as an ASCII text file in the form of the file named Sequence_Listing.txt, which was created on Oct. 21, 2016, and is 8301 bytes, which is incorporated by reference herein.

SEQ ID NO: 1 is a conserved portion of the first α-helical trimerization domain of CD74.

SEQ ID NO: 2 is an exemplary peptide of the conserved portion of the first α-helical trimerization domain of CD74.

SEQ ID NO: 3 is a conserved portion of the second α-helical trimerization domain of CD74.

SEQ ID NO: 4 is an exemplary peptide of the conserved portion of the second α-helical trimerization domain of CD74.

SEQ ID NO: 5 is a conserved portion of the third α-helical trimerization domain of CD74.

SEQ ID NOs: 6 and 7 are sequences from the N-terminal portion of the trimerization domain from human CD74.

SEQ ID NO: 8 is a sequence from the N-terminal portion of the trimerization domain from mouse CD74.

SEQ ID NO: 9 is a sequence from the C-terminal portion of the trimerization domain from human CD74.

SEQ ID NO: 10 is a sequence from the C terminal portion of the trimerization domain from mouse CD74.

SEQ ID NOs: 11-19 are exemplary peptide constructs including a first polypeptide covalently linked to a second polypeptide by a peptide linker.

SEQ ID NO: 20 is a portion of CD74 including residues that bind MIF.

SEQ ID NOs: 21 and 22 are exemplary MIF binding site peptides.

DETAILED DESCRIPTION

Multiple sclerosis (MS) and its murine model, experimental autoimmune encephalomyelitis (EAE), are chronic, debilitating autoimmune diseases of the central nervous system (CNS) characterized by extensive demyelination and axonal damage. One of the key cytokines thought to drive the early inflammatory stage of MS to a chronic progressive phase is Macrophage Migration Inhibitory Factor (MIF-1), the first described cytokine/chemokine. MIF-1 levels are increased in MS and have been implicated as a marker of clinical worsening in MS and as a requirement for disease progression in EAE. A potent biological construct called RTL1000 and a second generation derivative, DRα1-MOG-35-55, that bind tightly to the MIF-1 receptor, CD74, and competitively inhibit MIF-1 binding and downstream signaling were previously developed (Vandenbark et al., *J. Autoimmun.* 40:96-110, 2013; Meza-Romero et al., *J. Immunol.* 192:4164-4173, 2014; International Pat. Publ. WO 2013/103816; all of which are incorporated by reference herein). RTL1000 or DRα1-MOG-35-55 can treat mice with EAE after onset of clinical signs resulting in the inhibition of T cell and macrophage activation and migration into the CNS and reduced disease severity. RTL treatment was also found to enhance M2 macrophage/microglia cell numbers and to promote neuroprotection and reduction in the severity of acute and chronic EAE.

Using a docking program in silico, the inventors modeled binding interactions between the CD74 trimerization domain (CD74-TD) and MIF-1 as well as CD74-TD and RTL1000 (see also, Meza-Romero et al., *Metab. Brain Dis.* 31:249-255, 2016; incorporated herein by reference). These analyses revealed three binding sites on the MIF trimer that each was predicted to bind one CD74-TD trimer through interactions with two distinct five amino acid determinants. Surprisingly, predicted binding of one CD74 trimer to a single RTL1000 antagonist utilized the same two five-residue determinants, providing strong suggestive evidence in support of direct competition with the MIF binding regions on CD74. The structural modeling predicts a new MIF (CD74)$_3$ dodecamer that may possess increased MIF potency and the need for ~3-fold excess of RTL1000 to achieve full antagonism.

Recently, a second ligand for CD74 that is an ancestral functional homolog of MIF-1, called D-dopachrome tautomerase (DDT or MIF-2) was reported (Merk et al., *Cytokine* 59:10-17, 2012). The MIF-2 protein has only 35% homology with MIF-1, is expressed at equivalent levels in most tissues and has both common and distinct antigenic determinants. MIF-2 effects also require binding to CD74 and strongly overlap with those of MIF-1. Based on the modeling data provided herein, it is believed that a common region of CD74 binds to distinct but adjacent regions of the MIF-1 vs. MIF-2 homotrimers and that RTL1000 and DRα1-MOG-35-55 competitively block binding and downstream signaling of both MIF-1 and MIF-2. See also, Meza-Romero et al., *Cytokine* 88:62-70, 2016; incorporated by reference herein.

I. Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.). *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes and all molecular weight or molecular mass values, given for nucleic acids or polypeptides are approximate, and are provided for description. Although methods and materials similar or equivalent to those described herein can be used in the practice or testing of the present disclosure, suitable methods and materials are described below.

CD74: Also known as CD74 molecule, major histocompatibility complex, class II invariant chain or E. CD74 is a chaperone regulating antigen presentation for immune response. It is also a cell surface receptor for macrophage migration inhibitory factor (MIF).

Nucleic acid and protein sequences for CD74 are publicly available. For example, GenBank Accession Nos. NM_001025158, NM_004355, and NM_001025159 disclose exemplary human CD74 nucleic acid sequences, and GenBank Accession Nos. NP_001020329, NP_004346, and NP_001020330 disclose exemplary human CD74 amino acid sequences. Similarly, GenBank Accession Nos. NM_001042605 and NM_010545 disclose exemplary mouse CD74 nucleic acid sequences, and GenBank Accession Nos. NP_001036070 and NP_034675 disclose exemplary mouse CD74 amino acid sequences. Each of these sequences is incorporated herein by reference as present in GenBank on Oct. 16, 2015.

Conservative variants: A substitution of an amino acid residue for another amino acid residue having similar biochemical properties. "Conservative" amino acid substitutions are those substitutions that do not substantially affect or decrease an activity of a polypeptide, such as one of the disclosed polypeptides. A polypeptide can include one or more amino acid substitutions, for example 1-10 conservative substitutions, 2-5 conservative substitutions, 4-9 conservative substitutions, such as 1, 2, 5, 10, or more conservative substitutions. Specific, non-limiting examples of a conservative substitution include the following examples:

| Original Amino Acid | Conservative Substitutions |
|---|---|
| Ala | Ser |
| Arg | Lys |
| Asn | Gln, His |
| Asp | Glu |
| Gln | Asn |
| Cys | Ser |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Control: A "control" refers to a sample or standard used for comparison with an experimental sample. In some embodiments, the control is a sample obtained from a healthy subject or population of healthy subjects. In other embodiments, the control is a historical control or standard reference value or range of values (such as a previously tested control sample, such as a group of samples that represent baseline or normal values). In further examples, the control is from a subject prior to treatment (such as CD74 expression or activity level prior to treatment with one of the disclosed polypeptides).

Domain: A discrete part of an amino acid sequence of a polypeptide or protein that can be equated with a particular function. For example, the CD74 trimerization domain allows interaction with other CD74 monomers. Other CD74 domains function by interacting with MIF. The precise number of amino acids in the various CD74 domains varies depending on the species of mammal, as well as between classes of genes within a species. The critical aspect for selection of a sequence for use in a recombinant molecule is the maintenance of the domain function rather than a precise structural definition based on the number of amino acids. One of ordinary skill in the art will appreciate that domain function may be maintained even if somewhat less than the entire amino acid sequence of the selected domain is utilized. For example, a number of amino acids at either the amino or carboxy termini of the domain may be omitted without affecting domain function. The functional activity of a particular selected domain can be assessed in the context of the polypeptides disclosed herein (for example, as described in Example 1, below).

Effective amount: A dose or quantity of a specified compound sufficient to inhibit advancement, or to cause regression of a disease or condition, or which is capable of relieving symptoms caused by the disease or condition. For instance, this can be the amount or dose of one of the disclosed polypeptides required to treat or inhibit a disorder, such as an inflammatory and/or autoimmune disorder. In one embodiment, an effective amount is the amount that alone, or together with one or more additional therapeutic agents, induces the desired response in a subject, such as treating or inhibiting an inflammatory or autoimmune disorder or other disease or disorder.

Inflammation: A localized protective response elicited by injury to tissue that serves to sequester the inflammatory agent. Inflammation is orchestrated by a complex biological response of vascular tissues to harmful stimuli, such as pathogens, damaged cells, or irritants. It is a protective attempt by the organism to remove the injurious stimuli as well as initiate the healing process for the tissue. An inflammatory response is characterized by an accumulation of white blood cells, either systemically or locally at the site of inflammation. The inflammatory response can be measured by many methods well known in the art, such as the number of white blood cells, the number of polymorphonuclear neutrophils (PMN), a measure of the degree of PMN activation, such as luminal enhanced-chemiluminescence, or a measure of the amount of cytokines present. A primary inflammation disorder is a disorder that is caused by the inflammation itself. A secondary inflammation disorder is inflammation that is the result of another disorder. Inflammation can lead to a host of inflammatory diseases, including, but not limited to rheumatoid arthritis, osteoarthritis, inflammatory lung disease (including chronic obstructive pulmonary lung disease), inflammatory bowel disease (including ulcerative colitis and Crohn's Disease), periodontal disease, polymyalgia rheumatica, atherosclerosis, systemic lupus erythematosus, systemic sclerosis, Sjogren's Syndrome, asthma, allergic rhinitis, and skin disorders (including dermatomyositis and psoriasis) and the like. Autoimmune disorders which include an inflammatory component (including, but not limited to multiple sclerosis) can also be considered inflammatory disorders.

Inhibiting or treating a disease: "Inhibiting" a disease refers to inhibiting the full development of a disease, for example in a person who is known to have a predisposition to a disease such as an inflammatory or autoimmune disorder. Inhibition of a disease can span the spectrum from partial inhibition to substantially complete inhibition of the disease for example in a subject who has a disease or disorder or is at risk of developing a disease or disorder. In some examples, the term "inhibiting" refers to reducing or delaying the onset or progression of a disease. A subject to be administered with an effective amount of the pharmaceutical compound to inhibit or treat the disease or disorder can be identified by standard diagnosing techniques for such a disorder, for example, symptoms, basis of family history, or risk factor(s) to develop the disease or disorder. In contrast, "treatment" refers to a therapeutic intervention that ameliorates a sign or symptom of a disease or pathological condition after it has begun to develop.

Isolated: An "isolated" biological component (such as a nucleic acid, peptide or protein) has been substantially separated, produced apart from, or purified away from other biological components in the cell of the organism in which the component occurs, e.g., other chromosomal and extra-chromosomal DNA and RNA, and proteins. Nucleic acids, peptides and proteins which have been "isolated" thus include nucleic acids and proteins purified by standard purification methods. The term also embraces nucleic acids, peptides and proteins prepared by recombinant expression in a host cell, as well as chemically synthesized nucleic acids.

Linker: A molecule that covalently links two molecules (such as two polypeptides). Linkers (such as a peptide linker or a chemical linker) may be included in the disclosed polypeptides of the present disclosure for example between two alpha-helices of derived from the trimerization domain of CD74. Peptide linker sequences, which are often between 2 and 25 amino acids in length, are well known in the art and include, but are not limited to, the glycine(4)-serine spacer described by Chaudhary et al; (*Nature* 339, 394-397 (1989). Similarly, chemical linkers (such as thiol bonds or cross-linking agents) are well known in the art.

Macrophage Migration Inhibitory Factor (MIF): A protein expressed in a variety of tissues and cells, including leukocytes, corticotrophic pituitary cells, epithelial cells, endothelial cells, and neurons. MIF is considered a cytokine, hormone, and chemokine, and has enzymatic activity. It is a pro-inflammatory component of numerous autoimmune and inflammatory diseases. MIF is a homotrimer and binds to CD74 on MHC class II expressing cells. In some examples, MIF is referred to as "MIF-1."

Nucleic acid and protein sequences for MIF (MIF-1) are publicly available. For example, GenBank Accession No. NM_002415 discloses an exemplary human MIF nucleic acid sequence, and GenBank Accession No. NP_002406 discloses an exemplary human MIF amino acid sequence. Similarly, GenBank Accession No. NM_010798 discloses an exemplary mouse Mif nucleic acid sequence, and GenBank Accession No. NP_034920 discloses an exemplary mouse Mif amino acid sequence. Each of these sequences is incorporated herein by reference as present in GenBank on Oct. 19, 2016.

A second ligand for CD74 that is an ancestral functional homolog of MIF-1, called D-dopachrome tautomerase (DDT or MIF-2) has been identified (Merk et al., *Cytokine* 59:10-17, 2012). The MIF-2 protein has only 35% homology with MIF-1, is expressed at equivalent levels in most tissues, and has both common and distinct antigenic determinants. MIF-2 effects also require binding to CD74 and strongly overlap with those of MIF-1.

Nucleic acid and protein sequences for MIF-2 are publicly available. For example, GenBank Accession Nos. NM_001355 and NM_001084392 disclose exemplary human MIF-2 nucleic acid sequences, and GenBank Accession Nos. NP_001346 and NP_001077861 disclose exemplary human MIF-2 amino acid sequences. Similarly, GenBank Accession No. NM_010027 discloses an exemplary mouse Mif-2 nucleic acid sequence, and GenBank Accession No. NP_034157 discloses an exemplary mouse Mif-2 amino acid sequence. Each of these sequences is incorporated herein by reference as present in GenBank on Oct. 19, 2016.

Pharmaceutically acceptable carriers: The pharmaceutically acceptable carriers useful in this disclosure are conventional. *Remington: The Science and Practice of Pharmacy*, The University of the Sciences in Philadelphia, Editor, Lippincott, Williams, & Wilkins, Philadelphia, Pa., 21st Edition (2005), describes compositions and formulations suitable for pharmaceutical delivery of the polypeptides herein disclosed.

Polypeptide: A polymer in which the monomers are amino acid residues which are joined together through amide bonds. When the amino acids are alpha-amino acids, either the L-optical isomer or the D-optical isomer can be used, the L-isomers being preferred. The terms "polypeptide" or "protein" or "peptide" as used herein are intended to encompass any amino acid sequence and include modified sequences such as glycoproteins. The term "polypeptide" or "protein" or "peptide" is specifically intended to cover naturally occurring proteins, as well as those which are recombinantly or synthetically produced. It should be noted that the term "polypeptide" or "protein" includes naturally occurring modified forms of the proteins, such as glycosylated, phosphorylated, or ubiquinated forms.

Purified: The term purified does not require absolute purity; rather, it is intended as a relative term. Thus, for example, a purified peptide preparation is one in which the peptide or protein is more enriched than the peptide or protein is in its environment, for example within a cell or in a preparation. Preferably, a preparation is purified such that the protein or peptide represents at least 50% of the total peptide or protein content of the preparation. In some embodiments, a purified preparation contains at least 60%, at least 70%, at least 80%, at least 85%, at least 90%, at least 95% or more of the protein or peptide.

Recombinant: A recombinant nucleic acid or polypeptide is one that has a sequence that is not naturally occurring or has a sequence that is made by an artificial combination of two or more otherwise separated segments of sequence. This artificial combination is often accomplished by chemical synthesis or, more commonly, by the artificial manipulation of isolated segments of nucleic acids, e.g., by genetic engineering techniques. A recombinant polypeptide can also refer to a polypeptide that has been made using recombinant nucleic acids, including recombinant nucleic acids transferred to a host organism that is not the natural source of the polypeptide.

Sequence homology: Sequence homology between two or more nucleic acid sequences or two or more amino acid sequences, may be expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Methods of alignment of sequences for comparison are well known in the art. Various programs and alignment algorithms are described in: Smith & Waterman, Adv. Appl. Math. 2:482, 1981; Needleman & Wunsch, J. Mol. Biol. 48:443, 1970; Pearson & Lipman, Proc. Natl. Acad. Sci. USA 85:2444, 1988; Higgins & Sharp, Gene, 73:237-44, 1988; Higgins & Sharp, CABIOS 5:151-3, 1989; Corpet et al., Nuc. Acids Res. 16:10881-90, 1988; Huang et al. Computer Appls in the Biosciences 8, 155-65, 1992; and Pearson et al., Meth. Mol. Bio. 24:307-31, 1994. Altschul et al., J. Mol. Biol. 215:403-10, 1990, presents a detailed consideration of sequence alignment methods and homology calculations.

The NCBI Basic Local Alignment Search Tool (BLAST) (Altschul et al., J. Mol. Biol. 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site. BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75). For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, Comput. Appl. Biosci. 10:67-70). In addition, a manual alignment can be performed. Proteins with even greater similarity will show increasing percentage identities when assessed by this method, such as at least about 50%, 60%, 70%, 75%, 80%, 85%, 90%, 95%, 98%, 99%, or 100% sequence identity.

When aligning short peptides (fewer than around 30 amino acids), the alignment is to be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 50%, 60%, 70%, 75%, 80%, 85%, 90%, 95%, 98%, or 99% sequence identity to a protein. When less than the entire sequence is being compared for sequence identity, including a comparison of a dominant negative GW182 polypeptide, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

A pair of proteins or nucleic acids with 50%, 60%, 70%, 75%, 80%, 85%, 90%, 95%, 98%, or 99% identity to one another can be termed 'homologs,' particularly if they perform the same function as one another, even more particularly if they perform the same function to substantially the same degree, and still more particularly if they perform the same function substantially equivalently. One of skill in the art in light of this disclosure, particularly in light of the Examples below, would be able to determine without undue experimentation whether or not a given protein or nucleic acid sequence with 50%, 60%, 70%, 75%, 80%, 85%, 90%, 95%, 98%, or 99% identity to the sequences listed herein is a homolog to the sequences listed herein. Homologs need not be the same length as the biological molecules listed herein and may include truncations (fewer amino acids or nucleotides) or extensions (more amino acids or nucleotides) than the biological molecules listed herein.

Subject: Living multi-cellular vertebrate organisms, a category that includes both human and non-human mammals.

Vector: A nucleic acid molecule allowing insertion of foreign nucleic acid without disrupting the ability of the vector to replicate and/or integrate in a host cell. A vector can include nucleic acid sequences that permit it to replicate in a host cell, such as an origin of replication. A vector can also include one or more selectable marker genes and/or other genetic elements. An expression vector is a vector that contains the necessary regulatory sequences to allow transcription and translation of the inserted nucleic acid(s). In some embodiments herein, the vector is a plasmid vector. In other embodiments, the vector is a viral vector.

II. CD74 Derived Polypeptides

Disclosed are isolated polypeptides that include an alpha helical portion of the CD74 trimerization domain (such as consensus sequences SEQ ID NO: 1 and SEQ ID NO: 3 or α-helical polypeptides SEQ ID NO: 2 or SEQ ID NO: 4) or that include a portion of the MIF binding domain of CD74 (such as SEQ ID NO: 6 or SEQ ID NO: 9

In some examples, the polypeptides can be a single isolated peptide, a mixture isolated polypeptides including of two or more of the disclosed polypeptides, a composition that includes two or more of the disclosed polypeptides joined by a linker, a polypeptide comprising additional protein domains, or any other combination. Examples of such polypeptides include SEQ ID NOs: 11-18.

In some embodiments, a single polypeptide is included in a composition, such as a polypeptide including the amino acid sequence of SEQ ID NO: 1 or SEQ ID NO: 3 (such as the amino acid sequence of SEQ ID NO: 2 or SEQ ID NO: 4). Any of the polypeptides disclosed herein are also contemplated as being included in a composition disclosed herein.

In other embodiments, a composition includes a mixture of two or more of the disclosed polypeptides. In one example, the composition includes a polypeptide including the sequence of SEQ ID NO: 1 and a polypeptide including the sequence of SEQ ID NO: 3. In another example, the composition includes a first polypeptide including the sequence of SEQ ID NO: 7 and a second polypeptide including the sequence of SEQ ID NO: 9. Other mixtures of polypeptides disclosed herein are also contemplated.

In some examples, the composition includes two peptides that are covalently linked by a chemical or peptide linker. Exemplary polypeptides that include a first and second polypeptide linked by a peptide linker include the polypeptides of SEQ ID NOs: 11-16. In another example, the composition includes SEQ ID NO: 7 and SEQ ID NO: 9 linked by a peptide linker, which in some examples, includes SEQ ID NOs: 17-19.

In some examples, any of the compositions disclosed herein may also include a polypeptide including the amino acid sequence of SEQ ID NO: 5.

In still further embodiments, the composition includes a first polypeptide that includes the sequence YGMHT (SEQ ID NO: 21), wherein the first polypeptide is 10-25 amino acids long (for examples 15-20 or 12-18 amino acids long, for example 10, 11, 12, 13, 14, 15, 16, 17, 18, 19, 20, 21, 22, 23, 24, or 25 amino acids) and a second polypeptide that includes the sequence RHSLE (SEQ ID NO: 22), wherein the second polypeptide is 8-20 amino acids long (such as 10-18 or 12-15 amino acids, for example 8, 9, 10, 11, 12, 13, 14, 15, 16, 17, 18, 19, or 20 amino acids).

The polypeptides can include deletion or addition of a few amino acids at the 5'- and/or 3'-end, such as addition or deletion of about 1-10 amino acids, such as addition or deletion of 1, 2, 3, 4, 5, 6, 7, 8, 9, or 10 amino acids from the N-terminal or C-terminal end or combinations thereof (such as a deletion from one end and an addition to the other end). The composition of the disclosed polypeptide may also vary outside of these parameters depending on the mammalian species and the particular CD74 molecule in question. One of ordinary skill in the art will appreciate that the precise numerical parameters of the amino acid sequence are less important than the maintenance of domain function (for example, MIF binding).

Also disclosed herein are nucleic acids encoding the disclosed polypeptides. In some examples, the peptide of SEQ ID NO: 2 is encoded by nucleotides 599-637 of NM_004355, the peptide of SEQ ID NO: 4 is encoded by nucleotides 662-712 of NM_004355, the peptide of SEQ ID NO: 5 is encoded by nucleotides 719-776 of NM_004355, the peptide of SEQ ID NO: 7 is encoded by nucleotides 566-617 of NM_004355, the peptide of SEQ ID NO: 9 is encoded by nucleotides 764-794 of NM_004355, and the peptide of SEQ ID NO: 11 is encoded by nucleotides 599-709 of NM_004355. One of ordinary skill in the art can identify additional nucleic acid sequences that encode these or the other disclosed polypeptides. For example, nucleic acid sequences that do not show a high degree of sequence identity may nevertheless encode similar amino acid sequences, due to the degeneracy of the genetic code. It is understood that changes in nucleic acid sequence can be made using this degeneracy to produce multiple nucleic acid molecules that all encode substantially the same protein.

Nucleic acid molecules encoding the disclosed polypeptides can be produced by standard methods, such as amplification by the polymerase chain reaction (PCR). Standard approaches for designing primers for amplifying nucleic acids encoding the disclosed polypeptides can be employed. Libraries suitable for the amplification of the disclosed polypeptides include, for example, cDNA libraries. Such libraries are available commercially, or can be prepared by standard methods. Thus, for example, constructs encoding the disclosed polypeptides can be produced by PCR using primers corresponding to the 5' and 3' ends of the CD74 trimerization domain. Following PCR amplification, the amplified nucleic acid molecule can be cloned into a standard cloning vector. In some embodiments, for example to facilitate convenient cloning or linkage of an antigenic determinant (discussed below), one or both of the primers used can include a suitable restriction enzyme site such that the al domain encoding fragment can be readily ligated with another nucleic acid following amplification and digestion with the selected restriction enzyme.

In some embodiments, disclosed herein are vectors including a nucleic acid that encodes one or more of the polypeptides of SEQ ID NOs: 1-19. In some examples, the disclosed polypeptide is expressed in prokaryotic or eukaryotic cells from a nucleic acid construct including one or more sequences that encode the polypeptide. Nucleic acid constructs for expressing the disclosed polypeptide can also include regulatory elements such as promoters, enhancers, and 3' regulatory regions, the selection of which will be determined based upon the type of cell in which the protein is to be expressed. The constructs are introduced into a vector suitable for expressing the polypeptide in the selected cell type.

Numerous prokaryotic and eukaryotic systems are known for the expression and purification of polypeptides. For example, heterologous polypeptides can be produced in prokaryotic cells by placing a strong, regulated promoter and an efficient ribosome binding site upstream of the polypeptide-encoding construct. Suitable promoter sequences include the beta-lactamase, tryptophan (trp), phage T7 and lambda P L promoters. Methods and plasmid vectors for producing heterologous proteins in bacteria or mammalian cells are described in Sambrook et al, *Molecular Cloning: A Laboratory Manual,* 2d ed., Cold Spring Harbor Laboratory Press, 1989; Sambrook et al., *Molecular Cloning: A Laboratory Manual,* 3d ed., Cold Spring Harbor Press, 2001; Ausubel et al, *Current Protocols in Molecular Biology,* Greene Publishing Associates, 1992 (and Supplements to 2000); and Ausubel et al., *Short Protocols in Molecular Biology: A Compendium of Methods from Current Protocols in Molecular Biology,* 4$^{th}$ ed., Wiley & Sons, 1999.

Suitable prokaryotic cells for expression of large amounts of proteins include *Escherichia coli* and *Bacillus subtilis.* Often, proteins expressed at high levels are found in insoluble inclusion bodies; methods for extracting proteins from these aggregates are described for example, by Sambrook et al. (2001, see chapter 15). Recombinant expression of the disclosed polypeptides in prokaryotic cells may alternatively be conveniently obtained using commercial systems designed for optimal expression and purification of fusion proteins. Such fusion proteins typically include a tag that facilitates purification. Examples of such systems include: the pMAL protein fusion and purification system (New England Biolabs, Inc., Beverly, Mass.); the GST gene fusion system (Amersham Pharmacia Biotech, Inc., Piscataway, N.J.); and the pTrcHis expression vector system (Invitrogen, Carlsbad, Calif.). Additional systems include the His6-tag (e.g., Roche Applied Science, Mannheim, Germany) or streptavidin binding peptide (e.g., Sigma-Aldrich, St. Louis, Mo.). For example, the pMAL expression system utilizes a vector that adds a maltose binding protein to the expressed protein. The fusion protein is expressed in *E. coli*. And the fusion protein is purified from a crude cell extract using an amylose column. If necessary, the maltose binding protein domain can be cleaved from the fusion protein by treatment with a suitable protease, such as Factor Xa. The maltose binding fragment can then be removed from the preparation by passage over a second amylose column.

The disclosed polypeptides can also be expressed in eukaryotic expression systems, including *Pichia pastoris, Drosophila,* Baculovirus and Sindbis expression systems produced by Invitrogen (Carlsbad, Calif.). Eukaryotic cells such as Chinese Hamster ovary (CHO), monkey kidney (COS), HeLa, *Spodoptera frugiperda,* and *Saccharomyces cerevisiae* may also be used to express the disclosed polypeptides. Regulatory regions suitable for use in these cells include, for mammalian cells, viral promoters such as those from CMV, adenovirus or SV40, and for yeast cells, the promoter for 3-phosphoglycerate kinase or alcohol dehydrogenase.

The transfer of DNA into eukaryotic cells is routine. The vectors are introduced into the recipient cells as pure DNA (transfection) by, for example, precipitation with calcium phosphate or strontium phosphate, electroporation, lipofection, DEAE dextran, microinjection, protoplast fusion, or microprojectile guns. Alternatively, the nucleic acid molecules can be introduced by infection with virus vectors. Systems are developed that use, for example, retroviruses, adenoviruses, or Herpes virus.

One or more of the disclosed polypeptides produced in mammalian cells can be extracted following release of the protein into the supernatant and can be purified using an immunoaffinity column prepared using appropriate antibodies such as anti-CD74 trimerization domain antibodies. Alternatively, the disclosed polypeptides can be expressed as a chimeric protein with, for example, β-globin. Antibody to β-globin is thereafter used to purify the chimeric protein. Corresponding protease cleavage sites engineered between the β-globin gene and the nucleic acid sequence encoding the disclosed polypeptides are then used to separate the two polypeptide fragments from one another after translation. One useful expression vector for generating β-globin chimeric proteins is pSG5 (Stratagene, La Jolla, Calif.).

Expression of the polypeptides in prokaryotic cells will result in polypeptides that are not glycosylated. Glycosylation of the polypeptides at naturally occurring glycosylation target sites may be achieved by expression of the polypeptides in suitable eukaryotic expression systems, such as mammalian cells. In other examples, the polypeptide can be modified (for example, utilizing site-directed mutagenesis) to include desired post-translational modification sites, such as one or more sites for N-linked glycosylation, phosphorylation, or other modifications.

Purification of the expressed protein is generally performed in a basic solution (typically around pH 10) containing 6M urea. Folding of the purified protein is then achieved by dialysis against a buffered solution at neutral pH (typically phosphate buffered saline at around pH 7.4).

III. Methods of Treating or Inhibiting Disorders

Disclosed herein are methods of treating or inhibiting disorders in a subject, including but not limited to inflammatory and/or autoimmune disorders. The disclosed methods include administering one or more of the disclosed polypeptides (such as one or more of SEQ ID NOs: 1-19) or a pharmaceutical composition including one or more of the polypeptides, to a subject.

In some embodiments, the methods include selecting a subject with a disorder for treatment and administering an effective amount of one or more of the disclosed polypeptides or a nucleic acid encoding one or more of the disclosed polypeptides to the subject. In some examples, the polypeptide is covalently linked to an antigenic determinant or peptide (such as those discussed above).

In some embodiments, the subject has an inflammatory and/or autoimmune disease or disorder, including but not limited to, systemic lupus erythematosus, Sjogren's syndrome, rheumatoid arthritis, type I diabetes mellitus, Wegener's granulomatosis, inflammatory bowel disease, polymyositis, dermatomyositis, multiple endocrine failure, Schmidt's syndrome, autoimmune uveitis, celiac disease, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondylitis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, rubulavirus, and Evan's syndrome. Additional inflammatory diseases include osteoarthritis, inflammatory lung disease (including chronic obstructive pulmonary lung disease), periodontal disease, polymyalgia rheumatica, atherosclerosis, systemic sclerosis, allergic rhinitis, and skin disorders (including dermatomyositis and psoriasis) and the like.

In other embodiments, the subject has a retinal disorder, such as a retinal degeneration, such as retinitis pigmentosa, cone-rod dystrophy, Leber congenital amaurosis, or a maculopathy (for example, age-related macular degeneration, Stargardt-like macular degeneration, vitelliform macular dystrophy (Best disease), Malattia Leventinese (Doyne's honeycomb retinal dystrophy), diabetic maculopathy, occult macular dystrophy, and cellophane maculopathy). In other examples, a retinal disorder includes a retinopathy, such as autoimmune retinopathy, diabetic retinopathy, or vascular retinopathy. In still further examples, a retinal disorder includes retinal detachment or glaucoma. Retinal disorders may be progressive (for example, retinal degeneration or glaucoma) or acute (for example, retinal detachment). In additional examples, the subject is a subject with uveitis or optic neuritis. In other embodiments, the subject has had a stroke (such as ischemic stroke or hemorrhagic stroke). In still further examples, the subject is a subject with substance addiction, for example, a subject with cognitive or neuropsychiatric impairment induced by substance addiction.

In some embodiments, a subject is administered a pharmaceutical composition comprising an effective amount of one or more of the disclosed polypeptides. Pharmaceutical compositions that include one or more of the disclosed polypeptides can be formulated with an appropriate solid or liquid carrier, depending upon the particular mode of administration chosen. The pharmaceutically acceptable carriers and excipients useful in this disclosure are conventional. See, e.g., *Remington: The Science and Practice of Pharmacy*, The University of the Sciences in Philadelphia, Editor, Lippincott, Williams, & Wilkins, Philadelphia, Pa., 21st Edition (2005). For instance, parenteral formulations usually include injectable fluids that are pharmaceutically and physiologically acceptable fluid vehicles such as water, physiological saline, other balanced salt solutions, aqueous dextrose, glycerol or the like. For solid compositions (e.g., powder, pill, tablet, or capsule forms), conventional nontoxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, pH buffering agents, or the like, for example sodium acetate or sorbitan monolaurate. Excipients that can be included are, for instance, other proteins, such as human serum albumin or plasma preparations.

The dosage form of the pharmaceutical composition will be determined by the mode of administration chosen. For instance, in addition to injectable fluids, topical, inhalation, oral and suppository formulations can be employed. Topical preparations can include eye drops, ointments, sprays, patches and the like. Inhalation preparations can be liquid (e.g., solutions or suspensions) and include mists, sprays and the like. Oral formulations can be liquid (e.g., syrups, solutions or suspensions), or solid (e.g., powders, pills, tablets, or capsules). Suppository preparations can also be solid, gel, or in a suspension form. For solid compositions, conventional non-toxic solid carriers can include pharmaceutical grades of mannitol, lactose, starch, or magnesium stearate. Actual methods of preparing such dosage forms are known, or will be apparent, to those skilled in the art.

In some examples, the pharmaceutical composition can be administered by any method that achieves its intended purpose. Amounts and regimens for the administration of the disclosed polypeptides thereof (or a nucleic acid encoding such polypeptides) can be determined by the attending clinician. Effective doses for therapeutic application will vary depending on the nature and severity of the condition to be treated, the particular polypeptide selected, the age and condition of the patient, and other clinical factors. Typically, the dose range will be from about 0.1 µg/kg body weight to about 100 mg/kg body weight. Other suitable ranges include doses of from about 100 µg/kg to about 50 mg/kg body weight, about 500 µg/kg to about 10 mg/kg body weight, or about 1 mg/kg to about 5 mg/kg body weight. The dosing schedule may vary from once a month to daily depending on a number of clinical factors, such as the subject's sensitivity to the protein. Examples of dosing schedules are about 1 mg/kg administered once a month, bi-weekly, once a week, twice a week, three times a week or daily; a dose of about 2.5 mg/kg once a week, twice a week, three times a week or daily; a dose of about 5 mg/kg once a week, twice a week, three times a week or daily; a dose of about 10 mg/kg once a week, twice a week, three times a week or daily; or a dose of about 30 mg/kg once a week, twice a week, three times a week or daily.

The pharmaceutical compositions that include one or more of the disclosed polypeptides can be formulated in unit dosage form, suitable for individual administration of precise dosages. In one specific, non-limiting example, a unit dosage can contain from about 1 ng to about 5 g of polypeptide (such as about 10 µg to 1 g or about 10 mg to 100 mg). The amount of active compound(s) administered will be dependent on the subject being treated, the severity of the affliction, and the manner of administration. Within these bounds, the formulation to be administered will contain a quantity of the active component(s) in amounts effective to achieve the desired effect in the subject being treated.

The disclosed polypeptides can be administered to humans or other animals on whose tissues they are effective in various manners such as topically, orally, intravenously, intramuscularly, intraperitoneally, intranasally, intradermally, intrathecally, subcutaneously, intraocularly, via inhalation, or via suppository. In one example, the compounds are administered to the subject subcutaneously. In another example, the compounds are administered to the subject intravenously. Treatment can involve monthly, bi-monthly, weekly, daily or multi-daily doses of compound(s) over a period of a few days to months, or even years.

The disclosed polypeptides can be included in an inert matrix for topical application. In some examples, the formulation can be injected into the eye, for example for intravitreal injection. As one example of an inert matrix, liposomes may be prepared from dipalmitoyl phosphatidylcholine (DPPC), such as egg phosphatidylcholine (PC). Liposomes, including cationic and anionic liposomes, can be made using standard procedures as known to one skilled in the art. Liposomes including the disclosed polypeptides can be applied topically, either in the form of drops or as an aqueous based cream, or can be injected intraocularly. In a formulation for topical application, the polypeptide is slowly released over time as the liposome capsule degrades due to wear and tear from the eye surface. In a formulation for intraocular injection, the liposome capsule degrades due to cellular digestion. Both of these formulations provide advantages of a slow release drug delivery system, allowing the subject to be exposed to a substantially constant concentration of the polypeptide over time. In one example, the polypeptide can be dissolved in an organic solvent such as DMSO or alcohol as previously described and contain a polyanhydride, poly(glycolic) acid, poly(lactic) acid, or polycaprolactone polymer. The disclosed polypeptides can be included in a delivery system that can be implanted at various sites in the eye, depending on the size, shape and formulation of the implant, and the type of transplant procedure. Suitable sites include but are not limited to the anterior chamber, anterior segment, posterior chamber, posterior segment, vitreous cavity, suprachoroidal space, subconjunctiva, episcleral, intracomeal, epicomeal and sclera.

In some examples, an effective amount (for example, a therapeutically effective amount) of the disclosed polypeptides can be the amount of the disclosed polypeptide necessary to treat or inhibit a disorder (such as an inflammatory and/or autoimmune disorder) in a subject. In other examples, a therapeutically effective amount of the disclosed polypeptides can be the amount of polypeptide necessary to treat or inhibit a retinal disorder, stroke, or disorders associated with substance addiction (such as cognitive or neuropsychiatric impairment resulting from substance addiction).

The present disclosure also includes combinations of one or more of the disclosed polypeptides with one or more other agents useful in the treatment of a disorder. In some examples, the compounds of this disclosure can be administered with effective doses of one or more therapies for inflammatory or autoimmune disorders, including but not limited to non-steroidal anti-inflammatory drugs, corticosteroids, methotrexate, anti-TNF compounds, mycophenolate, aminosalicylates, antibiotics, interferons, glatiramer acetate, antibody therapies (such as rituximab or milatuzumab), or immunosuppressant or immunomodulatory compounds.

In another example, the compounds of this disclosure can be administered in combination with effective doses of one or more therapies for retinal disorders, including but not limited to, gene therapy, vitamin or mineral supplements (such as vitamins A, C, and/or E, or zinc and/or copper), anti-angiogenic therapy (such as ranibizumab or bevacizumab), photocoagulation, photodynamic therapy, lutein or zeaxanthin, corticosteroids, or immunosuppressants.

Appropriate combination therapy for a particular disease can be selected by one of ordinary skill in the art. The term "administration in combination" or "co-administration" refers to simultaneous or concurrent administration (such as substantially simultaneous administration) and sequential administration of the active agents.

EXAMPLES

The following examples are illustrative of disclosed embodiments. In light of this disclosure, those of skill in the art will recognize that variations of these examples and other examples of the disclosed technology would be possible without undue experimentation. At least some of the data presented herein was published in Meza-Romero et al. (*Metab. Brain Dis.* 31:249-255, 2016), incorporated by reference herein in its entirety.

Example 1

CD74 Alpha Helix I and Alpha Helix 2 Synergistically Bind to Human MIF

Figure 1B:
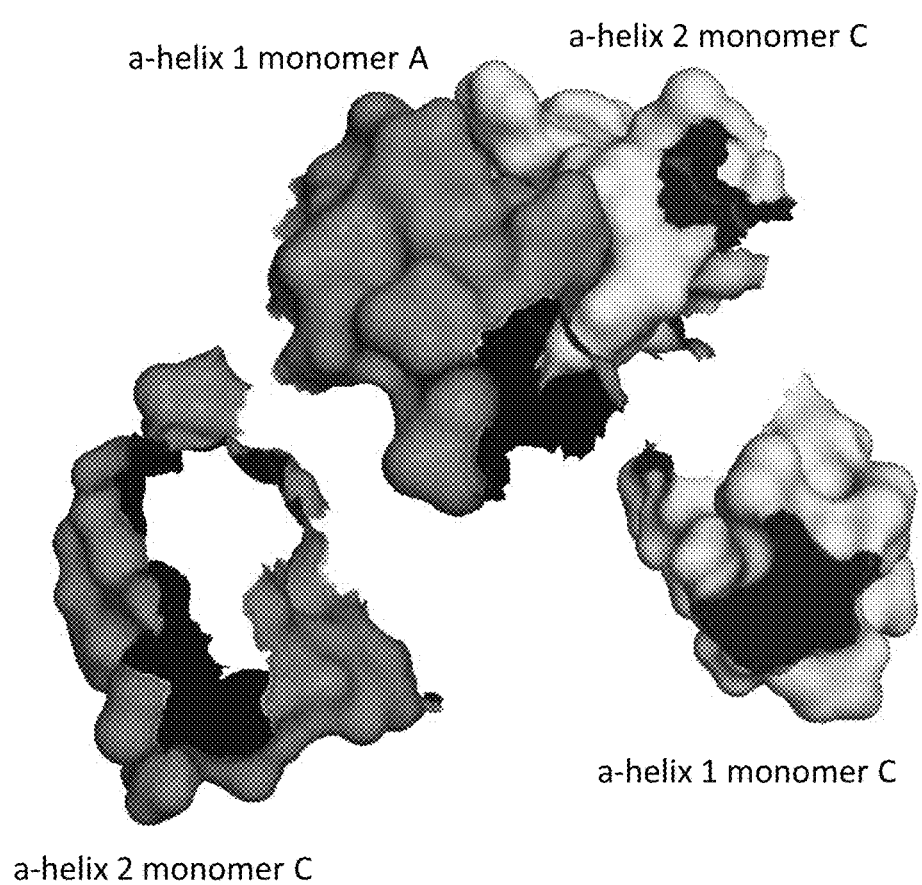
FIG. 1B is a representation of the alpha helix 1 and alpha helix 2 of the trimerization domain of CD74 in a surface area diagram. α-helix 1 on monomer A is parallel to α-helix 2 on monomer C. The α-helix 1 and α-helix 2 from different monomers are in intimate contact with each other.

The structure of the CD74 trimerization domain revealed that the α-helix 1 and α-helix 2 domains of the same monomer are separated by an unstructured region and therefore they are not in close contact to one another within the molecule. From the center of the α-helix 1 to the center of the α-helix 2 on the same monomer there is a distance of 18.8 Å. However, from the center of the α-helix 1 of monomer A to the center of the α-helix 2 of monomer C there is a distance of 7.1 Å (FIG. 1A). Therefore it is very possible that both α-helices from different monomers might make up the binding site for hMIF (FIG. 1B).

Figure 2A:
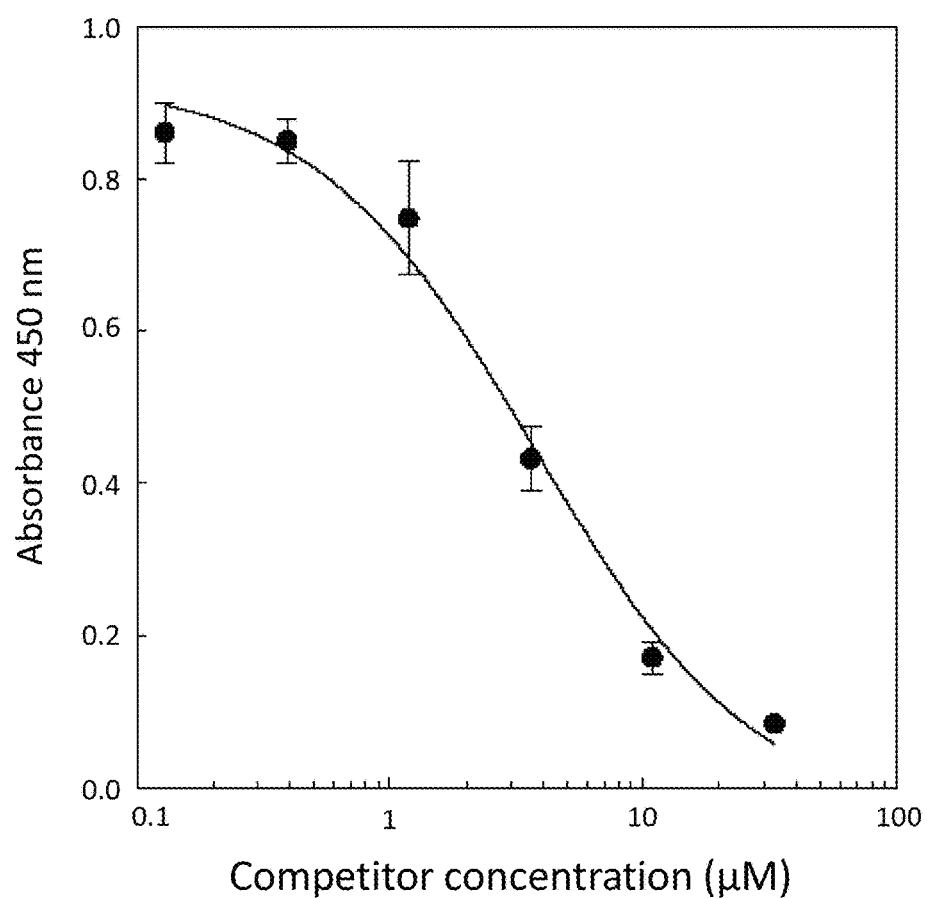
FIG. 2A is a plot showing a mixture of synthetic peptides representative of SEQ ID NO: 2 (α-helix 1) and SEQ ID NO: 4 (α-helix 2) blocked recombinant mouse full length (rmCD74) binding to human MIF.
Figure 2B:
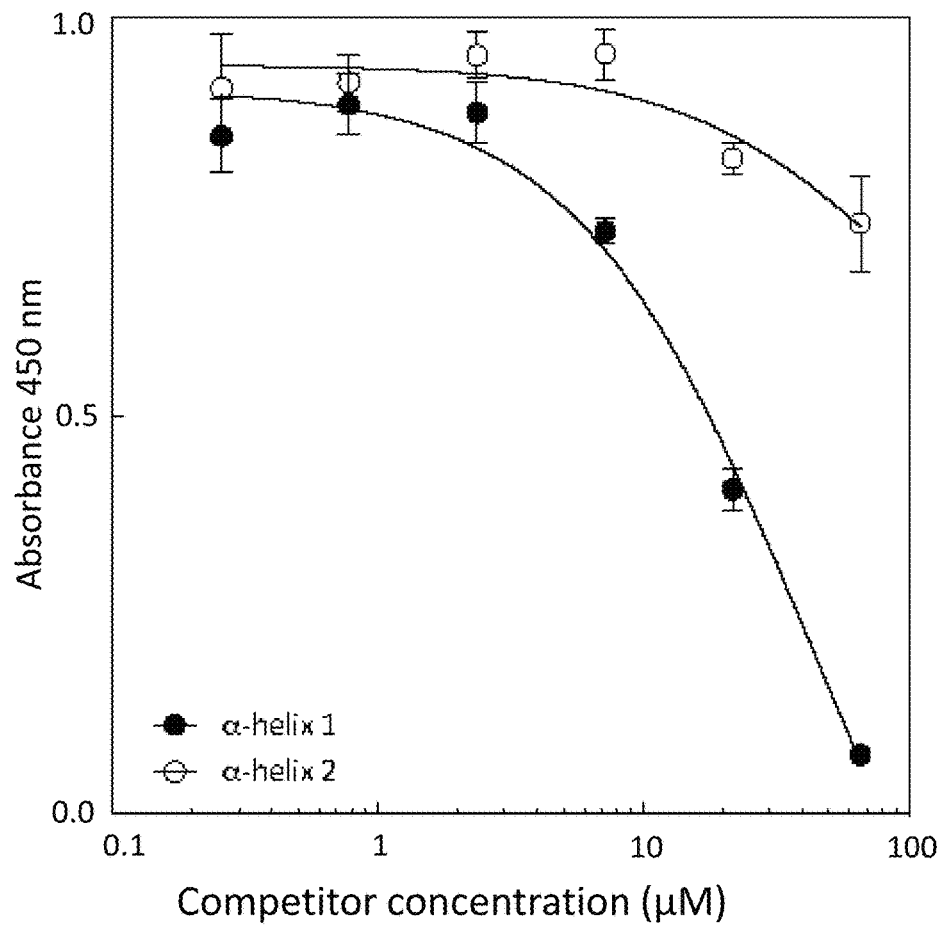
FIG. 2B is a plot showing that a purified population of SEQ ID NO: 2 (α-helix 1) is able to block recombinant mouse full length (rmCD74) binding to human MIF. A purified composition of SEQ ID NO: 4 (α-helix 2) blocked recombinant mouse full length (rmCD74) binding to human MIF to a lesser extent.

The ability of α-helix 1 and α-helix 2 peptides to compete with MIF for binding to CD74 was tested. Briefly, 50 µl of hMIF at a concentration of 0.5 µg/ml in PBS was coated onto ELISA plates for 2 hours at RT, washed 4 times with 3000 µl of PBS/0.0125% T20, blocked with 300 µl of 5% BSA in PBS, pH 7.4 for 2 hours at room temperature, and then a mixture of rmCD74 (constant concentration of 0.5 µg/ml) and competitor (SEQ ID NO: 2, SEQ ID NO: 4) at an initial concentration of 66 µM (33 µM each, mixed or 66 µM each, separately) in 5% BSA/PBS was added to the wells for 3 hours at room temperature to allow binding. Wells were thoroughly washed with PBS/T20 and the mAb PIN.1/anti-mIgG1-HRP (at 0.5 µg/ml in 5% BSA/PBS each) was used to detect the remaining rmCD74 bound to MIF. This mAb recognizes an epitope located at the N-terminus of the protein. Color was developed after adding 50 µl of TMB for 5 minutes and the reaction was stopped with 50 µl of 0.1N HCl. Data was first normalized and then analyzed using GraphPad Prism software. $IC_{50}$ were calculated by fitting the curve to a competition model involving a two-binding site equation. FIG. 2B shows that α-helix 1 (66 µM) blocks CD74 binding to hMIF but its effect increases 10-fold when α-helix 2 is also present at the total concentration of 33 µM each (FIG. 2A). The $IC_{50}$ of α-helix 1 plus α-helix 2 was 3.739 µM with an R square of 0.9777. The $IC_{50}$ of α-helix 1 alone was 41.80 µM (R square 0.9818) and of α-helix 2 alone was 114.2 µM (R square 0.7133).

Figure 3A:
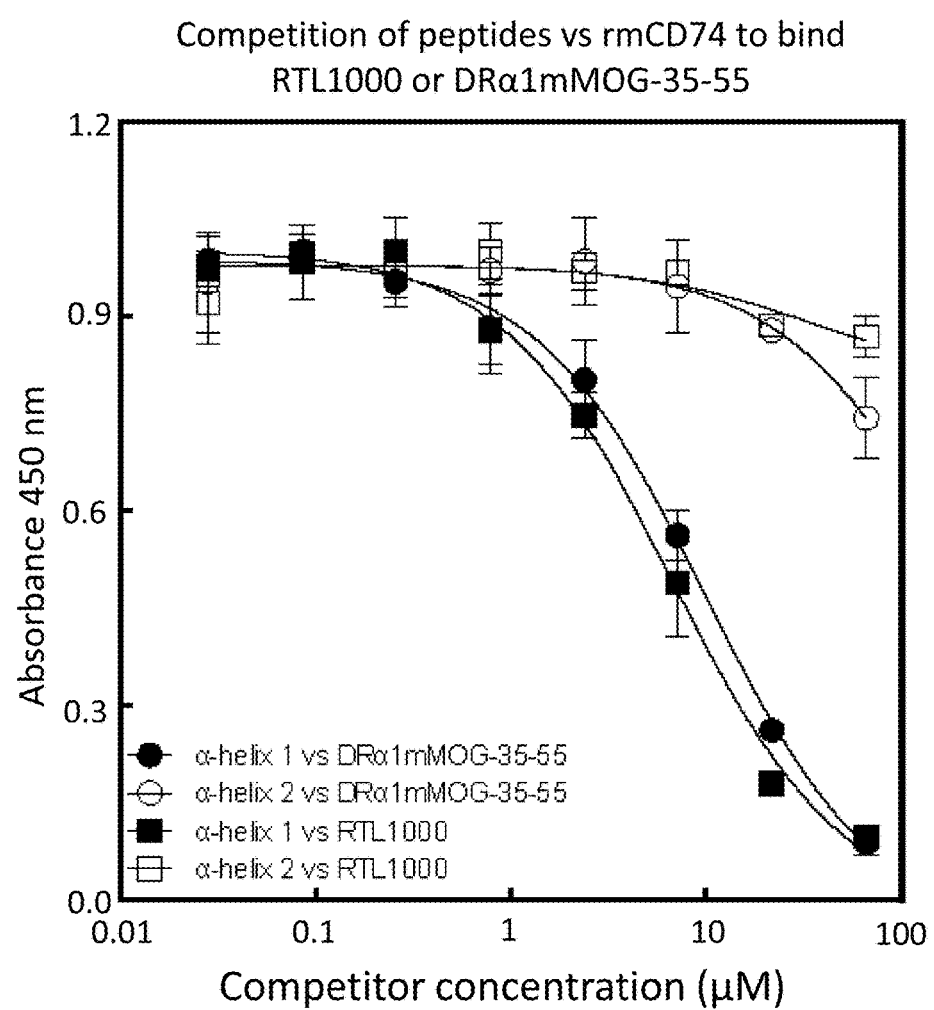
FIG. 3A is a plot showing that a purified peptide representative of SEQ ID NO: 2 (α-helix 1) is able to outcompete CD74 for binding to DRα1-mMOG-35-55 and RTL1000. A purified peptide representative of SEQ ID NO: 4 (α-helix 2) competes to a lesser extent.
Figure 3B:
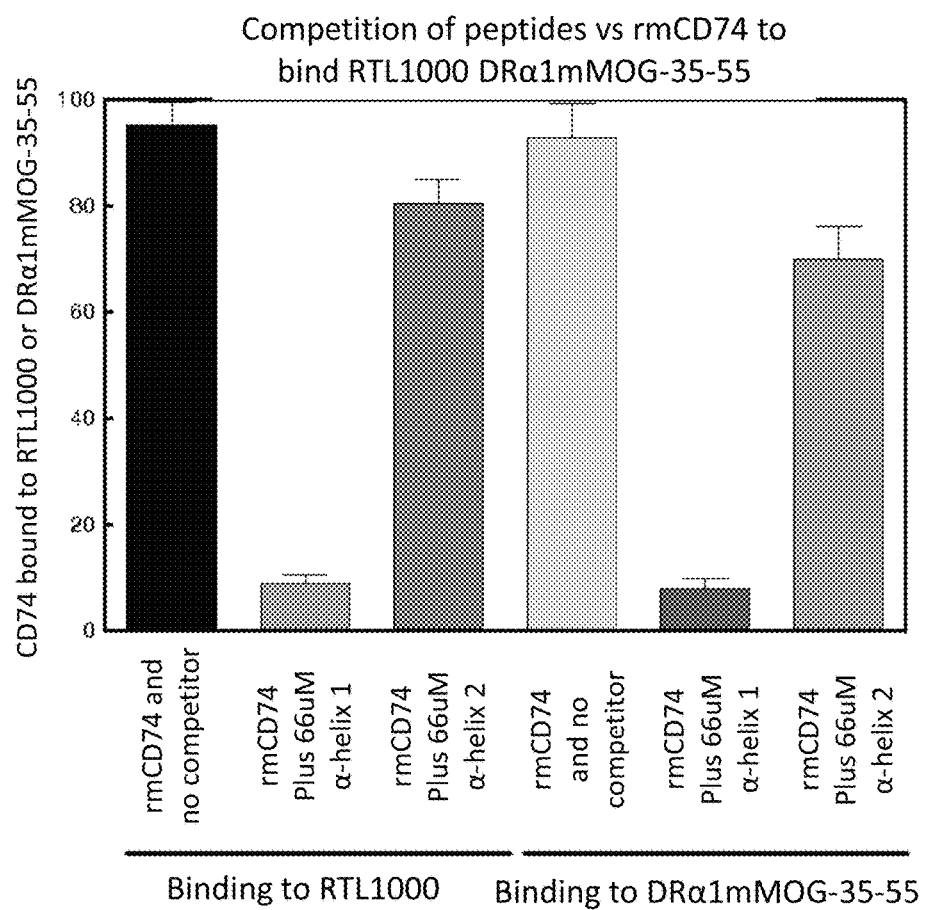
FIG. 3B is a bar graph quantifying the results of the plot in FIG. 3A at a constant concentration of SEQ ID NO: 2 or SEQ ID NO: 4 peptide.

Competition of peptides with rmCD74 for binding to RTL1000 or DRα1mMOG35-55 was also tested. Briefly, 50 µl of 1 µg/ml either RTL1000 or DRα1mMOG-35-55 were coated onto ELISA plates at 25° C. for 2 hours. Each well was washed 4 times with 300 µl of PBS/0.0125% Tween 20 (PBS/T20) to remove excess of protein and then blocked with 5% BSA/PBS at pH 7.4 (BSA/PBS) for 2 hours at the same temperature. Serial 1:2 dilutions of α-helix 1 or α-helix 2 (starting with a concentration of 66 µM, 50 µg/ml each) were prepared in rmCD74 (in BSA/PBS, 50 nM, 0.5 ug/ml) and added to the plate. Competition for the binding site was allowed for 3 hours at 25° C. and then unbound complexes were washed 4 times with PBS/T20. Remaining rmCD74 bound to RTL1000 or DRα1mMOG-35-55 was detected by the PIN.1/anti-mouse IgG1-HRP at 1 ul/ml of both in BSA/PBS for 1.5 hours at 25° C. and visualized by adding TMB substrate (50 µl, according to the manufacturer's instructions). Color development was stopped with 0.1N HCl and the plate was read at 450 nm in an ELISA plate reader. Data were normalized and fitted to a one-binding site model and competitor concentration was plotted against Absorbance at 450 nm to determine the $IC_{50}$ of each peptide competitor. All data were analyzed using Prism software (GraphPad). FIG. 3A shows the competition plot. FIG. 3B shows blocking of CD74/DRα1mMOG-35-55 or CD74/RTL1000 interactions with or without α-helix 1 or α-helix 2 peptides. Table 1 shows absolute and at 95% confidence interval values for $IC_{50}$, and R-square calculated from FIG. 3A using non-linear regression in the Prism software.

TABLE 1

| | IC50 values of α-helix 1 and α-helix 2 | | | |
|---|---|---|---|---|
| | α-helix 1 vs DRα1mMOG-35-55 | α-helix 2 vs DRα1mMOG-35-55 | α-helix 1 vs RTL 1000 | α-helix 2 vs RTL 1000 |
| LogIC50 | 1.002 | 2.222 | 0.8309 | 1.535 |
| IC50 | 10.05 | 166.6 | 6.775 | 34.27 |
| LogIC50 | 0.8946 to 1.110 | 0.5337 to 3.910 | 0.7069 to 0.9550 | 0.1254 to 2.944 |
| IC50 | 7.845 to 12.89 | 3.418 to 8121 | 5.092 to 9.015 | 1.335 to 880.0 |
| | α-helix 1 vs DRα1mMOG-35-55 | α-helix 2 vs DRα1mMOG-35-55 | α-helix 1 vs RTL 1000 | α-helix 2 vs RTL 1000 |
| R square | 0.9873 | 0.7391 | 0.9825 | 0.4625 |

Figure 4B:
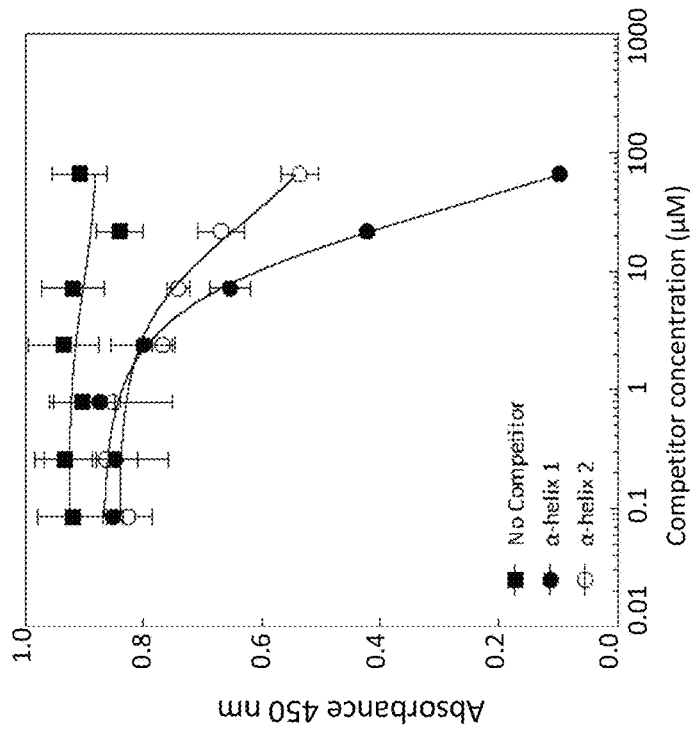
FIGS. 4A and 4B are a set of two plots showing that peptides representative of SEQ ID NO: 2 and SEQ ID NO: 4 in combination compete for binding of CD74 against DRα1-mMOG-35-55 better than either peptide alone.
Figure 4A:
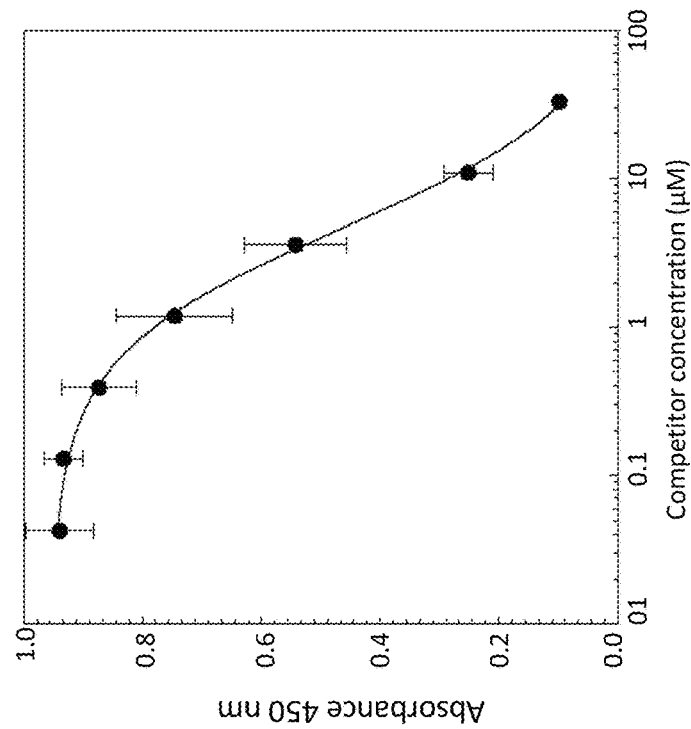

Human CD74 α-helix 1 and human CD74 α-helix 2 and block binding of rmCD74 to DRα1mMOG 35-55 and show synergistic cooperation (FIGS. 4A and 4B). As in the case of CD74 binding to hMIF, α-helix 1 and α-helix 2 together show a stronger activity to outcompete CD74 binding to DRα1mMOG-35-55. The $IC_{50}$ for the combined peptides is 4.75 µM in contrast to the 35 µM observed for the α-helix 1 peptide. At the same concentration, the α-helix 2 peptide did not have a significant effect on blocking CD74 binding to DRα1mMOG-35-55.

Example 2

Compositions Comprising CD74 Regions That Bind MIF

Figure 5:
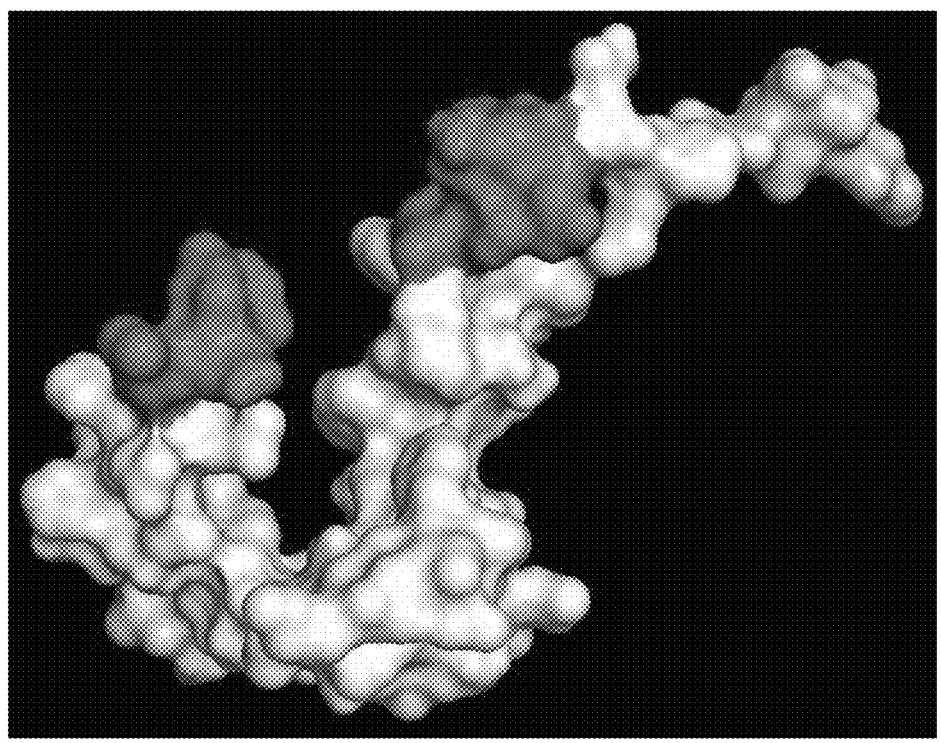
FIG. 5 is a representation of CD74 showing the residues that bind MIF in dark shading. The sequence of this region is: YGNMTEDHVMHLLQNADPLKVYPPLKGSFPENLRHLKNT METIDWKVFESWMHHWLLFEMSRHSLEQKPTDAPPK (SEQ ID NO: 20). Underlined residues are those shown in dark shading.

Docking analysis predicts binding of one CD74 Trimer to one monomer of the hMIF trimer. The MIF binding regions on CD74 include residues 118-YGNM-121 (amino acids 1-4 of SEQ ID NO: 21 and included in SEQ ID NO: 7 and SEQ ID NO: 8) and C-terminal residues 179-RHSL-182 (amino acids 1-4 of SEQ ID NO: 22 and included in SEQ ID NO: 9 and SEQ ID NO: 10) on each CD74 monomer (FIG. 5). The CD74 binding residues on MIF include both structural and biologically active regions that include the active site. Furthermore, the MIF binding regions on RTL1000 include both the 118-121 and 179-182 regions. Finally, a truncated CD74 that includes these regions was used to inhibit MIF activity (Leng et al., *J. Exp. Med.* 197:1467-1476, 2003, incorporated by reference herein).

Figure 6A:
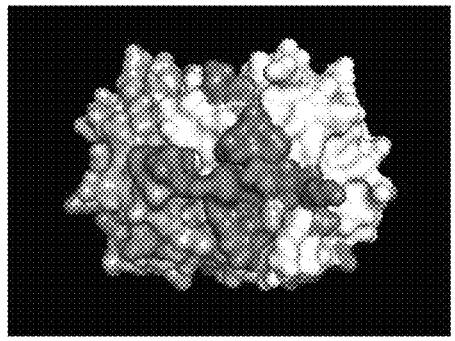
FIGS. 6A-6F show predicted binding regions of MIF-1 and MIF-2 for CD74-TD. Side view of MIF-1 (binding residues in blue and signaling residues in red, FIG. 6A) vs. MIF-2 (binding residues in orange, FIG. 6B). Side view of binding sites of MIF-1 (FIG. 6C) vs. MIF-2 (FIG. 6D) with overlay of N-terminal 118-YGNMT-122 (SEQ ID NO: 21) and C-terminal 179-RHSLE-183 (SEQ ID NO: 22) determinants from the CD74-TD. Bottom view showing positions of the predicted three separate binding sites for overlaid CD74-TD for one site in MIF-1 (FIG. 6E) vs. MIF-2 (FIG. 6F).
Figure 6B:
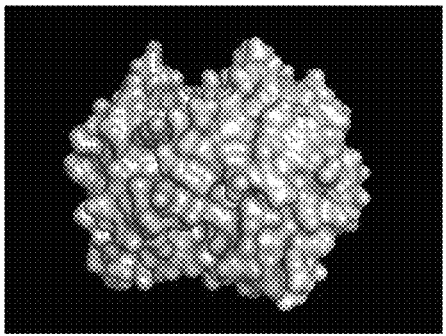
Figure 6C:
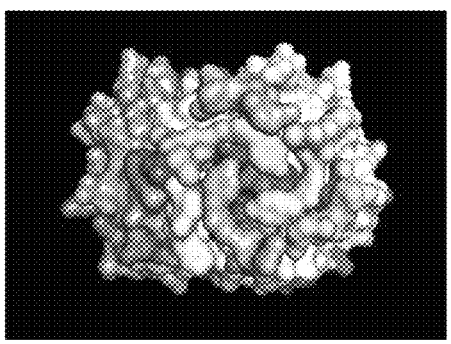
Figure 6D:
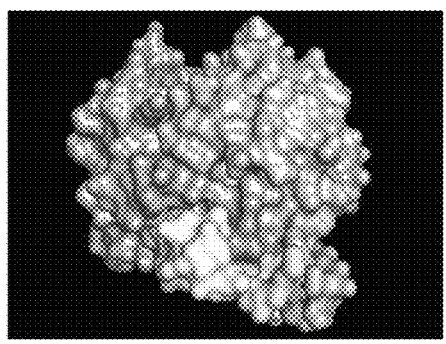
Figure 6E:
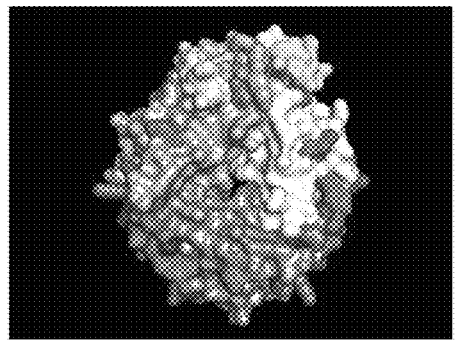
Figure 6F:
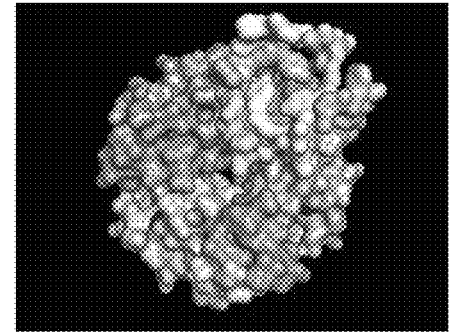

In addition, an initial evaluation of predicted binding interactions between MIF-2 and hCD74 has found that the CD74 binding region of MIF-2 is located on each monomer at the junction with the adjoining monomer, but is located in a different position nearer the bottom of the MIF-2 trimer than the MIF-1 binding region (FIG. 6A vs. 6B and 6E vs. 6F). Moreover, the binding involves the same 5-residue N-terminal 118-YGNMT-122 (SEQ ID NO: 21) and C-terminal 179-RHSLE-183 (SEQ ID NO: 22) determinants from the CD74-TD (FIG. 6C vs. 6D), lending strong support for MIF-2 as a functional homologue of MIF-1 and for the likely ability of RTL1000 and DRα1-MOG-35-55 to competitively inhibit binding and downstream activation by both MIF-1 and MIF-2. Note that the MIF-2 binding sites for the CD74-TD are rotated ~45° towards the bottom of the MIF-2 trimer and are offset by ~30° compared to the binding sites for MIF-1 that are located on the sides of the MIF-1 trimer. This topological difference in the location of the CD74 binding regions for MIF-2 vs. MIF-1 appear to be the result of an 8 amino acid insertion near the C terminus of MIF-2. Binding regions for both MIF-1 and MIF-2 are found at the interface of two monomers. The computer algorithms identified the same MIF-binding CD74 residues for both MIF-1 and MIF-2.

Example 3

Evaluation of Binding of CD74 Alpha Helix 1 and Alpha Helix 2 to Human MIF-2

Recently, a second ligand for CD74 that is an ancestral functional homolog of MIF, called D-dopachrome tautomerase (DDT) was reported. DDT has similar properties and functions as MIF, thus providing the rationale for the nomenclature of MIF-1 for MIF and MIF-2 for DDT. MIF-2 is present in many mammalian tissues and is highly conserved among species (Merk et al., *Cytokine* 59:10-17, 2012) Like MIF, DDT has vestigial enzymatic activity that catalyzes the tautomerization and decarboxylation of the non-naturally occurring substrate D-dopachrome to 5,6-dihydroxyindole (Odh et al., *Biochem. Biophys. Res. Commun.* 197:619-624, 1993; Sugimoto et al., *Biochemistry* 38:3268-3279, 1999) that does not appear to contribute to MIF's inflammatory properties. The human MIF-2 protein has only 34% identity with MIF-1 (27% similarity in mice; Merk et al., *Proc. Natl. Acad. Sci. USA* 108:E577-585, 2011), is expressed at equivalent levels in most tissues, with one report suggesting higher expression in murine brain (Esumi et al., *Mamm. Genome* 9:753-757, 1998), and has both common and distinct antigenic determinants. Like MIF-1, the MIF-2 protein forms a homotrimer with overlapping biological activities that depend on high affinity binding to CD74.

The binding of CD74 α-helices (such as SEQ ID NO: 2 and SEQ ID NO: 4) to MIF-2 is determined using the methods described in Example 1. In addition, the ability of these peptides to block binding of CD74 to RTL1000 and/or DRα1mMOG 35-55 is determined as described in Example 1.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

The invention claimed is:

1. A method of treating an autoimmune disorder comprising an inflammatory component in a subject, the method comprising administering to the subject an effective amount of a composition comprising:
   a first polypeptide comprising the sequence of SEQ ID NO: 7, wherein the first polypeptide is 17-25 amino acids long; and
   a second polypeptide comprising the sequence of SEQ ID NO: 9, wherein the second polypeptide is 10-20 amino acids long.

2. The method of claim 1, wherein the autoimmune disorder comprising an inflammatory component is multiple sclerosis, rheumatoid arthritis, or autoimmune uveitis.

3. The method of claim 1, wherein the composition is formulated for subcutaneous, intravenous, or intraocular administration.

4. The method of claim 1, wherein the subject is human.

5. The method of claim 1, wherein about 1 ng to about 5 g of polypeptide is administered to the subject.

6. The method of claim 1, wherein the composition comprises a first polypeptide consisting of SEQ ID NO: 7 and a second polypeptide consisting of SEQ ID NO: 9.

7. The method of claim 1, wherein the composition further comprises a linker polypeptide that covalently links the first polypeptide and the second polypeptide.

8. The method of claim 1, wherein the composition further comprises a pharmaceutically acceptable carrier.

9. A method of treating an autoimmune disorder comprising an inflammatory component in a subject, the method comprising administering to the subject an effective amount of a composition comprising a polypeptide of SEQ ID NO: 17, SEQ ID NO: 18, or SEQ ID NO: 19.

10. The method of claim 9, wherein the autoimmune disorder comprising an inflammatory component is multiple sclerosis, rheumatoid arthritis, or autoimmune uveitis.

11. The method of claim 9, wherein the composition is formulated for subcutaneous, intravenous, or intraocular administration.

12. The method of claim 9, wherein the subject is human.

13. The method of claim 9, wherein about 1 ng to about 5 g of polypeptide is administered to the subject.

14. The method of claim 9, wherein the composition further comprises a pharmaceutically acceptable carrier.

* * * * *

UNITED STATES PATENT AND TRADEMARK OFFICE
CERTIFICATE OF CORRECTION

| | |
|---|---|
| PATENT NO. | : 10,525,101 B2 |
| APPLICATION NO. | : 15/331612 |
| DATED | : January 7, 2020 |
| INVENTOR(S) | : Vandenbark et al. |

It is certified that error appears in the above-identified patent and that said Letters Patent is hereby corrected as shown below:

In the Specification

Column 1, Line 16, "Work resulting in this invention was supported by the United States government under the terms of Grant Number 5R01 NS047661, awarded by the National Institutes of Health, Grant Number RG-5068-A-6 and a Merit Review Grant awarded by the Department of Veterans Affairs. The United States government has certain rights to this invention." should read --This invention was made with government support under NS047661 awarded by National Institutes of Health. The government has certain rights in the invention.--.

Signed and Sealed this
Thirtieth Day of May, 2023

Katherine Kelly Vidal
*Director of the United States Patent and Trademark Office*

SEQUENCE LISTING

<160> NUMBER OF SEQ ID NOS: 22

<210> SEQ ID NO 1
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (2)..(2)
<223> OTHER INFORMATION: Xaa can be any naturally occurring amino acid

<400> SEQUENCE: 1

Thr Xaa Asp His Val Met His Leu Leu
1               5

<210> SEQ ID NO 2
<211> LENGTH: 13
<212> TYPE: PRT
<213> ORGANISM: Artificial Sequence
<220> FEATURE:
<223> OTHER INFORMATION: Synthetic peptide

<400> SEQUENCE: 2

Thr Glu Asp His Val Met His Leu Leu Gln Asn Ala Asp
1               5                   10

<210> SEQ ID NO 3
<211> LENGTH: 15
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 3

Lys Gly Ser Phe Pro Glu Asn Leu Xaa His Leu Lys Asn Xaa Met
1               5                   10                  15

<210> SEQ ID NO 4
<211> LENGTH: 17
<212> TYPE: PRT
<213> ORGANISM: Artificial Sequence
<220> FEATURE:
<223> OTHER INFORMATION: Synthetic peptide

<400> SEQUENCE: 4

Lys Gly Ser Phe Pro Glu Asn Leu Arg His Leu Lys Asn Thr Met Glu
1               5                   10                  15

Thr

<210> SEQ ID NO 5
<211> LENGTH: 20
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (10)..(10)
<223> OTHER INFORMATION: Xaa can be any naturally occurring amino acid

```
<220> FEATURE:
<221> NAME/KEY: misc_feature
<222> LOCATION: (19)..(20)
<223> OTHER INFORMATION: Xaa can be any naturally occurring amino acid

<400> SEQUENCE: 5

Trp Lys Val Phe Glu Ser Trp Met Lys Xaa Trp Leu Leu Phe Glu Met
1               5                  10                  15

Ser Ser Xaa Xaa
            20

<210> SEQ ID NO 6
<211> LENGTH: 15
<212> TYPE: PRT
<213> ORGANISM: Artificial Sequence
<220> FEATURE:
<223> OTHER INFORMATION: Synthetic peptide

<400> SEQUENCE: 6

Pro Met Gln Asn Ala Thr Lys Tyr Gly Asn Met Thr Glu Asp His
1               5                  10                  15

<210> SEQ ID NO 7
<211> LENGTH: 17
<212> TYPE: PRT
<213> ORGANISM: Artificial Sequence
<220> FEATURE:
<223> OTHER INFORMATION: Synthetic peptide

<400> SEQUENCE: 7

Pro Met Gln Asn Ala Thr Lys Tyr Gly Asn Met Thr Glu Asp His Val
1               5                  10                  15

Met

<210> SEQ ID NO 8
<211> LENGTH: 17
<212> TYPE: PRT
<213> ORGANISM: Artificial Sequence
<220> FEATURE:
<223> OTHER INFORMATION: Synthetic peptide

<400> SEQUENCE: 8

Pro Val Lys Asn Val Thr Lys Tyr Gly Asn Met Thr Gln Asp His Val
1               5                  10                  15

Met

<210> SEQ ID NO 9
<211> LENGTH: 10
<212> TYPE: PRT
<213> ORGANISM: Artificial Sequence
<220> FEATURE:
<223> OTHER INFORMATION: Synthetic peptide

<400> SEQUENCE: 9

Met Ser Arg His Ser Leu Glu Gln Lys Pro
1               5                  10

<210> SEQ ID NO 10
<211> LENGTH: 11
<212> TYPE: PRT
<213> ORGANISM: Artificial Sequence
<220> FEATURE:
<223> OTHER INFORMATION: Synthetic peptide

<400> SEQUENCE: 10
```

-continued

Met Ser Lys Asn Ser Leu Glu Glu Lys Lys Pro
1               5                   10

<210> SEQ ID NO 11
<211> LENGTH: 37
<212> TYPE: PRT
<213> ORGANISM: Artificial Sequence
<220> FEATURE:
<223> OTHER INFORMATION: Synthetic peptide

<400> SEQUENCE: 11

Thr Glu Asp His Val Met His Leu Leu Gln Asn Ala Asp Pro Leu Lys
1               5                   10                  15

Val Tyr Pro Pro Leu Lys Gly Ser Phe Pro Glu Asn Leu Arg His Leu
            20                  25                  30

Lys Asn Thr Met Glu
        35

<210> SEQ ID NO 12
<211> LENGTH: 41
<212> TYPE: PRT
<213> ORGANISM: Artificial Sequence
<220> FEATURE:
<223> OTHER INFORMATION: Synthetic peptide

<400> SEQUENCE: 12

Thr Glu Asp His Met His Leu Leu Gln Asn Ala Asp Gly Gly Gly Gly
1               5                   10                  15

Ser Leu Val Pro Arg Gly Ser Gly Gly Gly Ser Phe Pro Glu Asn
            20                  25                  30

Leu Arg His Leu Lys Asn Thr Met Glu
        35                  40

<210> SEQ ID NO 13
<211> LENGTH: 37
<212> TYPE: PRT
<213> ORGANISM: Artificial Sequence
<220> FEATURE:
<223> OTHER INFORMATION: Synthetic peptide

<400> SEQUENCE: 13

Thr Glu Asp His Val Met His Leu Leu Gln Asn Ala Asp Gly Gly Gly
1               5                   10                  15

Gly Ser Ser Gly Gly Gly Gly Ser Phe Pro Glu Asn Leu Arg His Leu
            20                  25                  30

Lys Asn Thr Met Glu
        35

<210> SEQ ID NO 14
<211> LENGTH: 39
<212> TYPE: PRT
<213> ORGANISM: Artificial Sequence
<220> FEATURE:
<223> OTHER INFORMATION: Synthetic peptide

<400> SEQUENCE: 14

Thr Glu Asp His Val Met His Leu Leu Gln Asn Ala Asp Gly Ser Gly
1               5                   10                  15

Gly Gly Thr Gly Gly Gly Ser Gly Gly Ser Phe Pro Glu Asn Leu Arg
            20                  25                  30

His Leu Lys Asn Thr Met Glu
        35

<210> SEQ ID NO 15
<211> LENGTH: 38
<212> TYPE: PRT
<213> ORGANISM: Artificial Sequence
<220> FEATURE:
<223> OTHER INFORMATION: Synthetic peptide

<400> SEQUENCE: 15

Ser Phe Pro Glu Asn Leu Arg His Leu Lys Asn Thr Met Glu Gly Ser
1               5                   10                  15

Gly Gly Gly Thr Gly Gly Ser Gly Thr Glu Asp His Val Met His
            20                  25                  30

Leu Leu Gln Asn Ala Asp
        35

<210> SEQ ID NO 16
<211> LENGTH: 36
<212> TYPE: PRT
<213> ORGANISM: Artificial Sequence
<220> FEATURE:
<223> OTHER INFORMATION: Synthetic peptide

<400> SEQUENCE: 16

Ser Phe Pro Glu Asn Leu Arg His Leu Lys Asn Thr Met Glu Gly Gly
1               5                   10                  15

Gly Gly Ser Ser Gly Gly Gly Thr Glu Asp His Val Met His Leu Leu
            20                  25                  30

Gln Asn Ala Asp
        35

<210> SEQ ID NO 17
<211> LENGTH: 36
<212> TYPE: PRT
<213> ORGANISM: Artificial Sequence
<220> FEATURE:
<223> OTHER INFORMATION: Synthetic peptide

<400> SEQUENCE: 17

Pro Met Gln Asn Ala Thr Lys Tyr Gly Asn Met Thr Glu Asp His Val
1               5                   10                  15

Met Gly Gly Gly Gly Ser Ser Gly Gly Gly Met Ser Arg His Ser Leu
            20                  25                  30

Glu Gln Lys Pro
        35

<210> SEQ ID NO 18
<211> LENGTH: 33
<212> TYPE: PRT
<213> ORGANISM: Artificial Sequence
<220> FEATURE:
<223> OTHER INFORMATION: Synthetic peptide

<400> SEQUENCE: 18

Pro Met Gln Asn Ala Thr Lys Tyr Gly Asn Met Thr Glu Asp Gly Gly
1               5                   10                  15

Gly Gly Ser Ser Gly Gly Gly Met Ser Arg His Ser Leu Glu Gln Lys
            20                  25                  30

Pro

<210> SEQ ID NO 19
<211> LENGTH: 37
<212> TYPE: PRT

```
<213> ORGANISM: Artificial Sequence
<220> FEATURE:
<223> OTHER INFORMATION: Synthetic peptide

<400> SEQUENCE: 19

Pro Val Lys Asn Val Thr Lys Tyr Gly Asn Met Thr Gln Asp His Val
1               5                   10                  15

Met Gly Gly Gly Gly Ser Ser Gly Gly Gly Met Ser Lys Asn Ser Leu
            20                  25                  30

Glu Glu Lys Lys Pro
        35

<210> SEQ ID NO 20
<211> LENGTH: 75
<212> TYPE: PRT
<213> ORGANISM: Artificial Sequence
<220> FEATURE:
<223> OTHER INFORMATION: Synthetic peptide

<400> SEQUENCE: 20

Tyr Gly Asn Met Thr Glu Asp His Val Met His Leu Leu Gln Asn Ala
1               5                   10                  15

Asp Pro Leu Lys Val Tyr Pro Pro Leu Lys Gly Ser Phe Pro Glu Asn
            20                  25                  30

Leu Arg His Leu Lys Asn Thr Met Glu Thr Ile Asp Trp Lys Val Phe
            35                  40                  45

Glu Ser Trp Met His His Trp Leu Leu Phe Glu Met Ser Arg His Ser
        50                  55                  60

Leu Glu Gln Lys Pro Thr Asp Ala Pro Pro Lys
65                  70                  75

<210> SEQ ID NO 21
<211> LENGTH: 5
<212> TYPE: PRT
<213> ORGANISM: Artificial Sequence
<220> FEATURE:
<223> OTHER INFORMATION: Synthetic peptide

<400> SEQUENCE: 21

Tyr Gly Asn Met Thr
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic peptide

<400> SEQUENCE: 22

Arg His Ser Leu Glu
1               5
```